United States Patent [19]
Lassila et al.

[11] Patent Number: 5,371,288
[45] Date of Patent: Dec. 6, 1994

[54] BRANCHED ALKYL-CONTAINING AMINOBENZAMIDES AS CHAIN EXTENDERS IN POLYURETHANE-UREA ELASTOMERS

[75] Inventors: Kevin R. Lassila, Allentown; Jeremiah P. Casey, Emmaus, both of Pa.

[73] Assignee: Air Products and Chemicals, Inc., Allentown, Pa.

[21] Appl. No.: 227,840

[22] Filed: Apr. 13, 1994

[51] Int. Cl.$^5$ .................... C07C 237/34; C08G 8/10; C08G 8/32
[52] U.S. Cl. ........................ 564/157; 528/64
[58] Field of Search ............. 564/157; 528/64

[56] References Cited

U.S. PATENT DOCUMENTS

| | | | |
|---|---|---|---|
| 3,188,302 | 6/1965 | Lorenz | 260/77.5 |
| 3,428,610 | 2/1969 | Klebert | 260/75 |
| 3,736,350 | 5/1973 | Meckel | 260/471 |
| 3,761,509 | 9/1973 | Lesher | 260/471 |
| 3,846,351 | 11/1974 | Huffaker et al. | 260/2.5 |
| 3,932,360 | 1/1976 | Ceranrowski | 260/77.5 |
| 4,218,543 | 8/1980 | Weber et al. | 521/51 |
| 4,222,955 | 9/1980 | Chung et al. | 260/465 |

FOREIGN PATENT DOCUMENTS 2227888 9/1988 Australia .

OTHER PUBLICATIONS

Baron, et al, "On the Use of Trimethylene Glycol Di--p-aminobenzoate as a Curing Agent for Polyurethane Elastomers", Appl. Polym. Sci., vol. 20 pp. 285-286 1976.

*Primary Examiner*—Peter O'Sullivan
*Attorney, Agent, or Firm*—Mark L. Rodgers; William F. Marsh

[57] ABSTRACT

N,N'-Di-(branched alkyl)-alkylenediamine-bis-p-aminobenzamides are useful as chain extenders in the manufacture of polyurethane-urea elastomers. These compositions have remarkably uniform reactivities but can be varied structurally to achieve a range of processibility characteristics by altering the melting points of the chain extenders. The preferred compounds melt in a range of 50° to 175° C. while exhibiting $t_{5000}$ reactivities of about four minutes. The combination of processing characteristics, reactivities and physical properties of the elastomer products offers advantages not available in commonly used diamine chain extenders of the prior art.

13 Claims, No Drawings

BRANCHED ALKYL-CONTAINING AMINOBENZAMIDES AS CHAIN EXTENDERS IN POLYURETHANE-UREA ELASTOMERS

FIELD OF THE INVENTION

This invention relates to bis-p-aminobenzamides containing branched alkyl groups on the amide nitrogens. In another aspect it relates to the use of such compounds as chain extenders in the manufacture of polyurethane-urea elastomers.

BACKGROUND OF THE INVENTION

Polyurethane-urea elastomers are widely used in industry to fabricate molded products. These elastomers are typically formed by reacting an organic polyisocyanate with a compound having a molecular weight between 400 and 10,000 containing at least two Zerewitenoff active hydrogen atoms, such as a polyhydroxyl compound, and an aromatic diamine chain extending agent. Alternatively, the chain extender is reacted with an isocyanate-terminated polyurethane prepolymer. Such prepolymers are well known in the art. In the molding operation the rate of reaction of the chain extender, or curative, and the processibility of the reacting composition is critical. If the reaction proceeds too fast, the composition will set up or gel before the mold can be completely filled. On the other hand, if the reaction is too slow, cycle times become too long and the cost of the operation is excessive. Finding the right curative for polyurethane-urea elastomers in a particular molding operation has been the subject of intensive research in this field for many years.

Three techniques have been used to reduce the reactivity of aromatic diamines in order to produce polyurethane-urea elastomer molding formulations with improved processibility. One technique involves incorporating organic substituents on the aromatic ring to hinder sterically the amine functionality. Klebert, U.S. Pat. No. 3,428,610 (1969) and Weber et al., U.S. Pat. No. 4,218,543 (1980) describe taking this approach to the problem, the latter patent also discussing the importance of reaction rates in the so called "one-shot" reaction injection molding (RIM) systems where the polyisocyanate, polyhydroxyl compound and aromatic polyamine are all combined at once rather than using a prepolymer.

A second technique involves adding an alkyl substituent to the amine nitrogen which both sterically hinders the amine group and reduces the number of active hydrogens. An example of this approach is given by Huffaker et al, U.S. Pat. No. 3,846,351 (1974) with N,N'-dialkyl-p-phenylenediamine. The third technique for reducing activity of an aromatic diamine is through electronic deactivation of the ring. Meckel et al., U.S. Pat. No. 3,736,350 (1973) take this approach by introducing ester and halogen or alkoxy groups onto the ring.

Lorenz, U.S. Pat. No. 3,188,302 (1965) describes a diamine curative which takes advantage of both steric hindrance and electronic deactivation to reduce its reactivity. Representative of such material is 4,4'-methylene-bis(2-chloroaniline) (which has been widely used in the art and is known by its shorthand name "MoCA". MoCA has the additional advantage of remaining liquid for long periods in the supercooled state even though it has a relatively high melting point of 130° C. This enhances its processibility. Unfortunately, as pointed out by Baron et al., J. Appl. Polym. Sci., 20, pp.285-6 (1976) the Occupational Safety and Health Administration has placed MoCA on a list of suspected carcinogens thereby stimulating considerable research for a suitable "drop-in" replacement. Several candidates are described by Baron et. al. and in a related patent of Cerankowski et al., U.S. Pat. No. 3,932,360 (1976) as alkylene glycol di-p-aminobenzoates. These curatives are made by reacting p-nitrobenzoyl chloride with an alkylene or cycloalkylene diol followed by reduction of the nitro groups to amine. Preferably the diol contains an odd number of carbons, and more preferably 3 or 5 carbons. All species are said to possess reasonable supercooling properties with the best candidate compared with the commercial MoCA being 1,3-propanediol di-p-aminobenzoate. The curative derived from 1,2-propanediol is said to have given poor elastomers and was not a good MoCA substitute. Baron et al. further concluded that the reduced reactivity of these compounds is attributable to electronic rather than steric effects.

The search to replace MoCA, which for some molding operations is considered too slow, is illustrated by the '543 patent cited above and by Chung et al., U.S. Pat. No. 4,222,955 (1980) who describe diamino alkylbenzoates, alkylbenzonitriles and alkylene bis(amino alkylbenzoates) as polyurethane curatives which are slower reacting than prior aromatic diamines but faster than MoCA which frequently requires a catalyst to shorten its reaction time.

Bis-p-aminobenzamides have been known for over two decades as possible chain extenders for polyurethane elastomers. German Offen. DE 1962602 (1971) discloses N,N'-hexamethylene-bis-p-aminobenzamide as a chain extender for an isocyanate-containing prepolymer. Chain extenders of this type would be expected to be extremely high melting and difficult to process. Much more recently, Australian Patent Application No. 22278/88 (1989) disclosed a broad class of reactive thickeners for various polymeric materials, these thickeners containing aminobenzoic acid derivatives are included isocyanates. Polyurethanes are listed among the polymers that can be thickened, and both mono- and diaminobenzoic acid derivatives are included in the thickeners, including bis-aminobenzamides, with or without alkyl or aryl substituents on the amide nitrogens. Suitable amines include ortho-, meta- and para-aminobenzoic acid derivatives, with specific examples named including 1,6-hexamethylenediaminodi-p-aminobenzamide, 1,2-ethylenediamine-di-p-aminobenzamide and the corresponding o-aminobenzamides. Poor physical properties would be expected for polyurethane-ureas cured with orthosubstituted aromatic amines, and there is the possibility that such materials could undergo side reactions on curing due to cyclization reactions of the ortho substituents (see Baron et al., supra).

Lesher, U.S. Pat. No. 3,761,509 (1973) discloses N,N'-alkylenebis(benzamides) having straight or branched chain lower alkyl substituents on the amide nitrogens, but the only aminobenzamides permissible are alkyl or dialkyl substituted amines which would not be suitable chain extenders. These compounds are stated to have endocrinological properties.

SUMMARY OF THE INVENTION

We have found that by introducing branched alkyl groups onto the amide nitrogen atoms of N,N'-alkylenediamine-bis-p-aminobenzamides, excellent chain extenders for polyurethane-urea elastomers are obtained with short but adequate potlifes. In addition, by altering the degree and type of branching in these pendent alkyl groups and by introducing additional branching in the connecting alkylene group, the physical properties and processibility of these chain extenders can be modified without significantly affecting their reactivity. Consequently, the invention provides a convenient way to tailor chain extender characteristics for particular molding operations.

These chain extenders are novel compounds which can be identified as N,N'-di-(branched alkyl)-alkylenediamine-bis-p-aminobenzamides. These compounds exhibit a variety of melting points within the range of desirable melting points for such chain extenders with remarkably uniform reactivities, making them ideal for use in manufacturing polyurethane-urea elastomers by well known industrial procedures.

DETAILED DESCRIPTION OF THE INVENTION

Although alkylene-linked p-aminoarylene derivatives, such as MoCA and 1,3-propanediol-bis-p-aminobenzoate (see '302 and '360 patents, supra), are very popular commercial chain extenders for polyurethane-urea elastomers, there are molding functions where the reactivity of these compounds is too slow for the high production rates required for economical operation. Thus the secondary amine-linked p-aminobenzamides of this invention meet a real need in the art for moderately reactive chain extenders that can be structured to take advantage of a variety of processing characteristics. These compounds are N,N'-di-(branched alkyl)-alkylenediamine-bis-p-aminobenzamides which can be represented by the formula:

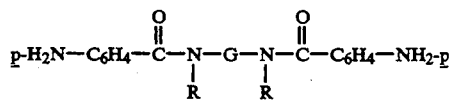

wherein G represents an alkylene group, preferably having 2 to 12 carbons, and each R represents a branched alkyl group, preferably having 4 to 8 carbons. Suitable alkylene groups include dimethylene, trimethylene, pentamethylene, hexamethylene, 1,12-dodecylene, and the like. Suitable branched alkyl groups include sec-butyl, neo-pentyl, 2-(4-methyl pentyl), 2,3-dimethyl butyl, and the like. Branching can also be introduced into the alkylene group as a means of further controlling melting point of the chain extender and, hence, processibility. Examples of branched alkylene groups include 2-methyl-1,5-pentylene, 2,5-dimethyl-1,6-hexylene, and the like. These materials exhibit reactivity which is higher than that observed in diol-linked p-aminobenzoic acid derivatives when used as curatives in polyurethane-urea formulations. The preferred chain extenders of the invention have surprisingly uniform reactivities indicated by $t_{5000}$ values of about four minutes.

Variation of the linking group and the pendent alkyl substituents provides a means of modifying the physical properties of the chain extender and the derived polyurethane-ureas. Specifically, increasing the length or the asymmetry of the connecting alkylene group decreases the melting point and, hence, increases the processibility of the chain extender. Also, increasing the asymmetry of the pendent branched alkyl substituent also decreases the melting point of the compound.

The use of these chain extenders in curing polyurethane-urea elastomers follows conditions and procedures which are well known in the art. The chain extenders are mixed with the isocyanate-containing compositions, preferably a prepolymer, and the mixture is quickly injected into a mold with the curing reaction taking place under pressure and at an elevated temperature. Ideally the melting point of the chain extender is such that high temperatures, e.g. above 200° C., are not required for efficient mixing and completely filling the mold. It is desirable, therefore, that these compounds have melting points below 200° C. and preferably between about 50° to 175° C.

The following examples are presented to illustrate specific embodiments of our invention and should not be construed to limit our invention unduly.

EXAMPLE 1

This example illustrates the preparation of N,N'-di-neo-pentyl-1,3-propanediamine-bis-p-aminobenzamide.

First the linking diamine was prepared. To a solution of pivaldehyde (24.4 mL) in absolute ethanol (25 mL) contained in the bottom portion of a 100 mL Parr autoclave was added dropwise via pipette neat 1,3-propanediamine (8.33 mL, 7.4 g, 100 mmol) over a 10 minute period. The temperature of the solution rose to about 45° C. The catalyst was added (5% palladium on carbon, 0.25 g), the reactor was sealed and pressure checked with nitrogen at 500 psi, and the reactor was purged of air with nitrogen by three pressure vent cycles. The reactor was then heated to 85° C. and pressured to 400 psi with hydrogen. Hydrogen uptake was monitored by means of a regulated ballast. After 3 hours, hydrogen uptake ceased, and the reactor was cooled, vented, and purged with nitrogen. The catalyst was removed by filtration. Gas chromatographic (GC) analysis of this crude reaction product indicated that it was composed of 96.3% of the desired diamine. Removal of the solvent by rotary evaporation followed by short-path vacuum distillation provided a colorless, viscous liquid, 10.98 g (51%, there were transfer losses), with a boiling point of 60°–62° C. (0.8 mm Hg). Product identity as N,N'-di-neo-pentyl-1,3-propanediamine was confirmed by $^1$H and $^{13}$C NMR spectroscopy and mass spectrometry.

The linking diamine was then converted to the bis-p-nitrobenzamide. N,N'-Di-neo-pentyl-1,3-propanediamine (10.26 g, 47.9 mmol) and a NaOH solution prepared from 5.2 g of NaOH and 50 mL of water were charged to a 250 mL three-necked round-bottomed flask equipped with magnetic stirrer, thermometer, condenser, addition funnel, and nitrogen inlet. A two phase mixture resulted. p-Nitrobenzoyl chloride (17.8 g, 96.2 mmol) was dissolved in 150 mL of diethyl ether and placed in the addition funnel. This solution was added carefully over a period of approximately one hour. A precipitate formed. After the completion of the addition, the reaction mixture was stirred overnight at room temperature. The ether was removed, about 50 mL of water was added to the reaction mixture, and the solid product was collected by suction filtration. The crude product was recrystallized from 125 mL of 95% ethanol and dried overnight in a vacuum oven at 100° C. to afford 21.10 g (86%) of off-white product having a melting point of 137°–139° C. The identity of this product was confirmed by elemental analysis and by its conversion to the corresponding diamine as follows.

A 100 mL autoclave was charged with the N,N'-di-neo-pentyl-1,3-propanediamine-bis-p-nitrobenzamide (10 g, 19.5 mmol), a catalyst of 5% palladium on carbon (0.25 g), and 95% ethanol (50 mL). The reactor was purged and pressure checked, then heated to 90° C. under 33 psi of hydrogen. When the contents had reached the reaction temperature, the pressure was increased to 500 psi with hydrogen. Hydrogen uptake was complete in 10 minutes. The reaction mixture was cooled to room temperature and the catalyst removed by filtration through Celite ®, an analytical grade filter agent composed of diatomaceous earth, (Celite Corporation). The solvent was removed by rotary evaporation, and the white product was dried under vacuum over the weekend. The resulting material weighed 8.27 g (94%) and had a melting point of 151°–154° C. The identity of the product as N,N'-di-neo-pentyl-1,3-propanediamine-bis-p-aminobenzamide was confirmed by $^1$H and elevated temperature $^{13}$C NMR spectroscopy.

EXAMPLE 2

This example illustrates the preparation of N,N'-di-sec-butyl-1,3-propanediamine-bis-p-aminobenzamide.

First the linking diamine was prepared with the use of a solvent. Into a 100 mL Parr autoclave were placed 1,3-propanediamine (7.4g, 100 mmol), 2-butanone (18.72 g, 260 mmol), absolute ethanol (25 mL) and a catalyst of 5% palladium on carbon (0.25g). No exotherm was noted upon mixing. The reactor was sealed and pressure checked at 500 psi, and purged of air as in Example 1. The reaction mixture was heated to 85° C. and pressured to 500 psi with hydrogen. The mixture was allowed to react for a total of 3.5 hours. The reaction mixture was then cooled to room temperature, the reactor vented and purged with nitrogen, and the catalyst was removed by filtration through Celite. The solvent was removed by rotary evaporation to afford 17.8 g of crude material which had a GC flame ionization detector (FID) area percent assay of 98.6% for the desired product. The product was purified by vacuum distillation through a 4 inch by 0.5 inch internal diameter vigreux column. A 0.43 g forecut was discarded. The product, 15.69 g (85%), had a boiling point of 55°–57° C. (0.35torr).

The above procedure was repeated, but without using a solvent, which is the preferred synthesis method. A two liter autoclave was charged with 1,3-propanediamine (385mL), 2-butanone (850 mL) and the Pd-C catalyst (5.0 g). This mixture was hydrogenated using the procedure of Example 1 at 500 psi and 85° C. for 20 hours. The catalyst was removed by vacuum filtration through Celite and the crude product was purified by distillation through a 12 inch by 1 inch i.d. Propack ® (metal packing) column. Early fractions contained 2-butanone as well as hydrogenated aldol condensation products. A total of 773 g of product of greater than 99.5% purity was isolated (90% yield). The identity of the product was confirmed by elemental analysis, mass spectrometry, and $^1$H and $^{13}$C NMR spectroscopy. This material was then converted to the bis-p-nitrobenzamide.

To a two liter three-necked round-bottomed flask equipped with overhead stirrer, addition funnel, and reflux condenser was added NaOH (41.6 g, 1.04 mol) and 400 mL of water. To this solution was added N,N'-di-sec-butyl-1,3-propanediamine (74.47 g, 0.40 mol). p-Nitrobenzoyl chloride (147.97 g, 0.80 mol) was dissolved in 1200 mL of ether and added rapidly over about 20 minutes via the addition funnel to the stirred mixture containing the diamine. The rate of addition was such that the mixture refluxed rapidly. At the completion of the addition no precipitate had formed as in reactions with other diamines. The reaction mixture was stirred for an additional hour during which time a precipitate formed. The condenser was replaced with a distillation head and the ether was removed by distillation. The solid was collected, washed thoroughly with water, and recrystallized from 1300 mL of ethanol and dried in a vacuum oven to afford 175.95 g (91%) of product having a melting point of 108°–112° C. The identity of the product was confirmed by elemental analysis and elevated temperature $^1$H and $^{13}$C NMR spectroscopy. The product was then hydrogenated to the aminobenzamide derivative.

A two liter autoclave was charged with N,N'-di-sec-butyl-1,3-propanediamine-bis-p-nitrobenzamide (174.0 g, 0.36 mol), a catalyst of 5% Pd on carbon (5.0 g), and 95% ethanol (1000 mL). The reactor was purged and pressure checked as in Example 1 and pressurized to 394 psi with hydrogen, heated to 80° C., and then pressurized to 500 psi with hydrogen. After two hours under these conditions, hydrogen uptake was complete and the contents of the reactor was cooled to room temperature and removed by suction. The catalyst was filtered as in Example 1 and solvent removed by rotary evaporation. The crude product (150.86 g) was recrystallized from 3300 mL of toluene, cooled in an ice bath, and collected by vacuum filtration. After drying under vacuum at 50° C. for 65 hours, the product weighed 143.09 g (94%) and had a melting point of 150°–153° C. Identity of the product was confirmed by elemental analysis and by $^1$H and $^{13}$C NMR spectroscopy as N,N'-di-sec-butyl-1,3-propanediamine-bis-p-aminobenzamide.

EXAMPLE 3

This example describes the preparation of N,N'-di-2-(4-methylpentyl)-1,3-propanediamine-bis-p-aminobenzamide.

First the linking diamine was prepared. A 100 mL Parr autoclave was charged with 1,3-propanediamine (7.4g, 100 mmol), methylisobutyl ketone (26 g, 260 mmol), ethanol (20 mL), and 0.25 g of the 5% Pd-C catalyst as used in Example 1. No exotherm was noted upon mixing. The reactor was sealed, purged and pressure checked as in Example 1. The reaction mixture was then heated to about 85° C. and pressured to 500 psi with hydrogen. The reaction mixture was stirred under these conditions for 20 hours, cooled to room temperature, vented and purged with nitrogen. The reaction product was filtered as in Example 1 to remove catalyst, and the solvent was removed by rotary evaporation to produce 24.0 g of crude product. GC analysis of this material indicated that it was composed primarily of the desired diamine (98.2 FID GC area percent). The crude product was purified by vacuum distillation through a 4"×0.5" vigreux column. Two forecuts weighing 1.27 g were discarded. The major fraction of 21.3 g (88%) had a boiling point of 82° C. (0.35 torr). The identity of the product as N,N'-di-2-(4-methylpentyl)-1,3- propanediamine was confirmed by elemental analysis, mass spectrometry, and $^1$H and $^{13}$C NMR spectroscopy.

This product (12.1 g, 50 mmol) was added to a 250 mL three-necked round-bottomed flask equipped with condenser, addition funnel and overhead stirrer, to which had been previously added NaOH (5.2 g) dissolved in 50 mL of water. Then a solution of p-nitrobenzoyl chloride (18.5 g, 100 mmol) dissolved in ether (150 mL) was added over 15 minutes through the addition funnel. After completion of the reaction, the mixture was stirred for an additional 45 minutes by which time no precipitate had formed. The mixture was transferred to a separatory funnel and the organic layer was washed with water and brine, dried over magnesium sulfate, filtered, and the solvent removed by rotary evaporation. The product was dried under vacuum (ambient temperature, 0.3 torr) to afford 25.2 g of product (98% yield). Identity of the product was confirmed by $^1$H and $^{13}$C NMR spectroscopy.

This product (10.0 g) was then hydrogenated by melting it on a steam bath and placing it in a 100 mL autoclave with 5% Pd-C catalyst (0.25 g) and 95% ethanol(50 mL). The hydrogenation was carried out as in Example 1 using 517 psi hydrogen and 88° C. Hydrogen uptake was complete in about 40 minutes. Catalyst and solvent were removed as in Example 1. The crude product was placed on the vacuum line overnight to afford 8.78 g (94%) of material having a melting point of 65°–80° C. Identity of the product as N,N'-di-2-(4-methylpentyl)-1,3-propanediamine-bis-p-aminobenzamide was confirmed by $^1$H and $^{13}$C NMR spectroscopy.

EXAMPLE 4

This example describes the preparation of N,N'-di-sec-butyl-1,6-hexanediamine-bis-p-aminobenzamide.

The linking diamine was prepared by charging hexamethylenediamine (11.6 g, 100 mmol), 2-butanone (18.7 g, 260 mmol), absolute ethanol (30 mL), and 5% Pd-C catalyst (0.25 g) to a 100 mL Parr autoclave. The reactor was pressure checked and purged as in Example 1, vented to atmospheric pressure and heated to 82° C. It was then pressurized to 520 psi with hydrogen and stirred overnight at these conditions. After 17 hours the reaction mixture was cooled to room temperature, vented and purged free of hydrogen. The catalyst was removed as in Example 1 and the solvent removed from the filtrate by rotary evaporation to afford 19.9 g of colorless liquid. GC analysis of this material indicated it to have 99.4% purity. It was further purified by vacuum distillation to yield 16.2 g of product (72%) having a boiling point of 96°–98° C. (0.5 torr).

The above procedure was repeated without a solvent using a two liter autoclave charged with 1,6-hexanediamine (468 g, 4.0 mol), 2-butanone (747 g, 10 mol) and 5.12 g of the catalyst. The reactor was purged as in Example 1 and pressurized to 360 psi with hydrogen. The reactor contents was heated to 92° C. while stirring at 500 rpm and allowed to react for 20 hours. The contents was then cooled and the reactor vented and purged with nitrogen. Catalyst was removed as in Example 1 and the product purified by vacuum distillation through a 12"×1" Propack column to give 843 g of material (93%) of 99.88% purity, having a boiling point of 160°–163° C. The identity of the product was confirmed by elemental analysis, mass spectrometry, and $^1$H and $^{13}$C NMR spectroscopy as N,N'-di-sec-butyl-1,6-hexanediamine.

This product (68.6 g, 0.3 mol) was reacted with p-nitrobenzoyl chloride (112.3 g, 0.6 mol) in a two phase ether/aqueous NaOH system in a procedure similar to that of Example 1 to produce 142 g of product (87%) which after recrystallization from ethanol had a melting point of 136°–137° C. Identity as N,N'-di-sec-butyl-1,3-propanediamine-bis-p-nitrobenzamide was confirmed by elemental analysis and $^1$H and $^{13}$C NMR spectroscopy. This product (130 g) was hydrogenated as in Example 3 to the corresponding diamine. Recrystallization from ethyl acetate/hexane produced 108 g of white powder having a melting point of 134°–137° C. The identity as N,N'-di-sec-butyl-1,6-hexanediamine-bis-p-aminobenzamide was confirmed by elemental analysis and $^1$H and $^{13}$C NMR spectroscopy.

EXAMPLE 5

This example describes the preparation of N,N'-di-sec-butyl-2-methyl-1,5-pentanediamine-bis-p-aminobenzamide.

The linking diamine was prepared by placing 2-methyl-1,5-pentanediamine (464 g, 4.0 mol), 2-butanone (748 g, 10.4 mol) and 5% Pd-C catalyst (5 g) in a two liter autoclave. A temperature increase to about 40° C. was noted. The vessel was purged and pressure checked at 700 psi and the reaction mixture was heated to 80° C. and pressured to 700 psi with hydrogen. After 11 hours hydrogen uptake ceased and after 21 hours the reaction vessel was cooled to room temperature, vented and purged with nitrogen. The catalyst was removed and the product purified as in the solventless run of Example 2 to provide 418 g of material of 99.8% purity and having a boiling point of 127° C. Identity of the product as N,N'-di-sec-butyl-2-methyl-1,5-pentanediamine was confirmed by elemental analysis and by $^1$H and $^{13}$C NMR spectroscopy.

This product was converted to the bis-p-nitrobenzamide derivative in a manner similar to that of the foregoing Examples and then hydrogenated to the corresponding p-aminobenzamide using a two liter Parr autoclave charged with N,N'-di-sec-butyl-2-methyl-1,5-pentanediamine-bis-p-nitrobenzamide (60 g), 5% Pd-C catalyst (1.48 g) and 1000 mL of 95% ethanol. After the pressure check and purging cycles, the reactor was pressurized to 305 psi with hydrogen and heated to 80° C. When the reactor contents had reached temperature, the vessel was pressurized to 500 psi with hydrogen. Hydrogen uptake was complete in 20 minutes, but the reactor was held under these conditions for an additional two hours. The contents were filtered to remove catalyst and solvent removed as in Example 1 to afford 45.29 g of crude product having a melting point of 58°–66° C. Further purification by drying under vacuum at 170° C. and 0.3 torr for 10 hours with stirring gave a product having a melting point of 85°–91° C. Identity of this product was N,N'-di-sec-butyl-2-methyl-1,5-pentanediamine-bis-p-aminobenzamide as confirmed by elemental analysis and $^1$H and $^{13}$C NMR spectroscopy.

COMPARATIVE EXAMPLE 6

To illustrate the benefits of alkyl branching on the amide nitrogen atoms of the compositions of the invention, a comparative run was made by preparing N,N'-dimethylethylenediamine-bis-p-aminobenzamide.

To a two liter three-necked round-bottomed flask equipped with overhead stirrer, addition funnel, condenser, and nitrogen inlet was added NaOH (29.5 g, 0.738 mol) and 280 mL of water. This solution was allowed to cool and N,N'-dimethylethylenediamine (25.0 g, 0.284 mol) was dissolved in the NaOH solution. p-Nitrobenzoyl chloride (105.1 g, 0.567 mol) was dissolved in about one liter of diethyl ether and placed in the addition funnel. The solution was added dropwise rapidly, the rate being limited by the rate at which the ether refluxed. The addition was complete in one hour. A solid had formed soon after the start of the addition, but this did not interrupt stirring. After the completion of the addition, the reaction mixture was allowed to cool to room temperature. The condenser was replaced with a vacuum distillation takeoff head and the ether was removed under vacuum. An additional 500 mL of water was added to the flask and the white solid was collected by vacuum filtration, washed twice with water, once with ethanol, and dried with suction overnight. The product, 104.3 g (95%), had a melting point of 187°–188° C. Identity was confirmed by $^1$H and $^{13}$C NMR spectroscopy.

A 100 mL autoclave was charged with N,N'-dimethylethylenediamine-bis-p-nitrobenzamide (11.58 g), 5% Pd-C catalyst (0.26 g), and 50 mL of 95% ethanol. After the usual pressure check and purge cycles, the reactor was pressurized to 92 psi with hydrogen and heated to 90° C. The pressure was increased to 500 psi and the stir rate was increased to the system's maximum. After 45 minutes, hydrogen uptake had ceased and the reactor contents was cooled to room temperature and filtered. The solvent was removed from the filtrate to afford on orange-white solid, 3.44 g (35%), having a melting point of 215°–217° C. Identity of the product as N,N'-dimethylethylenediamine-bis-p-aminobenzamide was confirmed by $^1$H and elevated temperature $^{13}$C NMR spectroscopy.

A comparison of the melting point of this compound with the melting points of the compounds of Examples 1 through 5 is given in Table 1.

TABLE I

| Example | Aklylene Group | Alkyl Group | MP °C. |
|---|---|---|---|
| 6 | dimethylene | methyl | 215–217 |
| 1 | trimethylene | neo-pentyl | 151–154 |
| 2 | trimethylene | sec-butyl | 150–153 |
| 3 | trimethylene | 2-(4-methylpentyl) | 65–80 |
| 4 | hexamethylene | sec-butyl | 134–137 |
| 5 | 2-methylpentamethylene | sec-butyl | 85–91 |

The above data show that the compound of Example 6 had an undesirably high melting point for efficient processibility as a chain extender in polyurethane-urea elastomers. On the other hand, the compounds of Examples 1 through 5 all had melting points well within an acceptable range. Moreover, the data show that these melting points can be significantly modified by altering the branching on the pendent branched alkyl groups on the amide nitrogens. Also, increasing the length of the connecting alkylene group and introducing branching on this group provides further melting point reduction. The ability to vary melting point in this manner provides a high degree of control over the processing characteristics of these chain extenders.

EXAMPLE 7

The reactivities of the chain extenders of Examples 2 through 5 were examined using the potlife test procedure described by Casey et al., *Proceedings of the SPI 28th Annual Technical/Marketing Conference*, pp. 218–223 (1984). The tests were performed by dissolving the chain extender (1 equivalent) in CAPA® 200, a polycaprolactone of 274 equivalent weight obtained from Interox, (1 equivalent) in a stainless steel test cup and preconditioning this mixture at 50° C. for one hour. The homogeneity of this mixture was ascertained, and Adiprene® L167, toluene diisocyanate (TDI) capped 1000 molecular weight polytetramethyleneglycol, Uniroyl, (2-equivalents) thermostatted at 50° C. was carefully layered on top. The test cup was placed in a thermostatted block on the test apparatus and a perforated plunger driven at constant pressure by a reciprocating air motor was activated. Frequency data for the plunger were stored on a minicomputer and later converted to relative viscosity. A plot of relative viscosity vs time was produced. The time required for the mixture to reach a relative viscosity of 5000 ($t_{5000}$) was recorded. The $t_{5000}$ value provides a concise reactivity comparison for various chain extenders.

For comparison $t_{5000}$ values were also obtained for a commercial chain extender, Polacure® 740M, the bis-p-aminobenzoate of 1,3-propanediol, Air Products and Chemicals, Inc., and comparable values were obtained from data available on three other known chain extenders, methylenedianiline (MDA), tetra-iso-propyl-methylenedianiline (TiPMDA), and di-iso-propyl-o-tolidine (DiPoT). The results are given in Table 2. The $t_{5000}$ values are an average of at least two determinations.

TABLE 2

| Chain Extender | $t_{5000}$ (min) |
|---|---|
| Polacure ® | 26.2 |
| Example 2 | 4.0 |
| Example 3 | 4.2 |
| Example 4 | 4.0 |
| Example 5 | 4.3 |
| TiPMDA | 3.0 |
| DiPoT | 1.8 |
| MDA | 0.7 |

The data of Table 2 show that the $t_{5000}$ values for the chain extenders of the invention are much less than that of MoCA, which has a value of 42 minutes, and were surprisingly less than the diol-linked materials of the prior art, namely 1,3-propanediol-bis-p-aminobenzoate, Polacure ®. This higher reactivity would be beneficial in many industrial applications by resulting in increased productivity. The reactivity of these curatives would make them attractive for certain reaction injection molding (RIM) operations. The fact that the $t_{5000}$ values for the invention are higher than for other commercial chain extenders, e.g. TiPMDA, DiPoT and MDA, shows that these new materials provide greater processing latitude than these aromatic diamines. They also exhibit a reactivity which is in a window not available in commonly used diamine chain extenders of the prior art. It is quite surprising that the reactivities of these chain extenders of the invention were almost identical ($t_{5000}$ values of about 4 minutes) in spite of the fact that they vary considerably in processibility as indicated by their melting points. This moderated reactivity would be beneficial for many operations by maximizing productivity while maintaining processibility.

EXAMPLE 8

This example examines physical properties of elastomers made with the compositions of the invention and compares them to compositions of the prior art. Plaques were cast by mixing the molten chain extender, either neat (1.0 equivalent), or as an admixture composed of 0.65 equivalents of chain extender and 0.35 equivalents of PolyTHF 650, a polytetramethylene glycol of 650 molecular weight made by BASF, with 1.05 equivalents of Airthane ® PET 95A prepolymer, a TDI-capped 1000 molecular weight polytetramethylene glycol containing less than 0.1% free TDI, manufactured by Air Products and Chemicals, Inc., at 70° C. and placing this material in a mold having inside dimensions of 6"×6"×⅛", preheated to 100° C. The material was pressed at 100° C. and about 15 tons, and cured in the mold until the part had developed sufficient mechanical strength for removal from the mold (about one hour). the material was then postcured at 100° C. for such a time that the total cure time was 16 hours. Defect-free pieces were cut from these plaques and their properties were measured according to ASTM procedures D-412-83 (Microtensile), D-624-81 (Die C Tear), and D-2240-81 (Durometer Hardness). Values taken were the average of three determinations. The results are set forth in Table 3.

TABLE 3

| Chain Extender | Shore A | Shore B | Tensile[a] | Tear[b] | Elongation[c] |
|---|---|---|---|---|---|
| MoCA | 93 | 42 | 5240 | 550 | 350 |
| Polacure ® | 97 | 32 | 5260 | 730 | 440 |
| Example 4 | 91 | 41 | 4100 | 500 | 710 |
| Polacure ®/T650 | 86 | 49 | 2240 | 420 | 350 |
| Example 4/T650 | 71 | 26 | 2420 | 210 | 470 |
| Example 2/T650 | 83 | 36 | 2860 | 230 | 420 |
| Example 5/T650 | 80 | 35 | 3550 | 210 | 520 |

[a]Pounds per square inch at break.
[b]Pounds per linear inch.
[c]Percent.

The data of Table 3 show that elastomers made with the chain extenders of this invention have physical properties which compare very well with polyurethane-urea elastomers form commercial formulations.

As can be seen from the foregoing Examples, the chain extenders of this invention are useful in the manufacture of polyurethane-urea elastomers which would meet requirements of the industry. In addition they offer a compromise between highly processible but slowly reacting diamines of the prior art which can suffer from limited productivity, and highly reactive diamines which have the disadvantage of poor processibility. The options of structural variation among the compositions of the invention provide a high degree of control over the processing characteristics of the chain extenders without significantly altering their reactivities.

Other advantages and features of our invention will be apparent to those skilled in the art from the foregoing disclosure without departing from the spirit or scope of our invention.

We claim:

1. N,N'-Di-(branched alkyl)-alkylenediamine-bis-p-aminobenzamide.

2. The composition of claim 1 wherein said alkylenediamine group contains 2 to 12 carbons.

3. The composition of claim 2 wherein each of said branched alkyl groups contains 4 to 8 carbons.

4. The composition of claim 3 wherein each of said branched alkyl groups is sec-butyl.

5. The composition of claim 3 wherein each of said branched alkyl groups is neo-pentyl.

6. The composition of claim 3 wherein each of said branched alkyl groups is 2-(4-methylpentyl).

7. The composition of claim 2 wherein said alkylenediamine group contains branching.

8. The composition of claim 7 wherein said alkylenediamine group is 2-methyl-1,5-pentanediamine.

9. The composition of claim 4 wherein said alkylenediamine group is 1,3-propanediamine.

10. The composition of claim 5 wherein said alkylenediamine group is 1,3-propanediamine.

11. The composition of claim 6 wherein said alkylenediamine group is 1,3-propanediamine.

12. The composition of claim 4 wherein said alkylenediamine group is 1,6-hexanediamine.

13. The composition of claim 4 wherein said alkylenediamine group is 2-methyl-1,5-pentanediamine.

* * * * *